United States Patent [19]
Aronson et al.

[11] Patent Number: 6,087,118
[45] Date of Patent: Jul. 11, 2000

[54] METHOD FOR DIAGNOSING ALZHEIMER'S DISEASE

[75] Inventors: Jeffrey K. Aronson, Oxford, United Kingdom; H. Asita de Silva, Kohuwala, Sri Lanka; David G. Grahame-Smith, Oxford, United Kingdom

[73] Assignee: Bristol-Myers Squibb Company, Princeton, N.J.

[21] Appl. No.: 09/262,772

[22] Filed: Mar. 4, 1999

[51] Int. Cl.$^7$ .............................. C12Q 1/56; C12Q 1/00
[52] U.S. Cl. .................. 435/13; 435/4; 424/529; 424/532
[58] Field of Search ............ 435/13, 4; 424/529, 424/532

[56] References Cited

U.S. PATENT DOCUMENTS

| | | | |
|---|---|---|---|
| 5,580,748 | 12/1996 | Alkon et al. | 435/13 |
| 5,705,401 | 1/1998 | Masters et al. | 435/4 |
| 5,778,893 | 7/1998 | Potter | 435/13 |

OTHER PUBLICATIONS

Fraser, S.P. et al, Ionic effects of the Alzheimer's disease β–amyloid precursor protein and its metabolic fragments, Trends Neurosci. 20, 67072 (1997).

Atwal, K., Med. Res. Rev. 12, 6, 579; N.S. Cook, Trends Pharmacol. Sci. 9, 21 (1988).

Marqueze, B. et al, Euro. J. Biochem., 169, 295, (1987).

Gimenez, G. et al. Proc. Natl. Acad. Sci., USA, 85, 3329 (1988).

Etcheberrigaray, R. et al, Potassium channel dysfunction in fibroblasts identifies patients with Alzheimer's disease, Proc. Natl. Acad. Sci., USA, 90, 8209–8213 (1993).

Etcheberrigaray, R. et al, Soluble β–amyloid induction of Alzheimer's phenotype for human fibroblast $K^{30}$ channel, Science, 264, 276–276 (1994).

*Primary Examiner*—Louise N. Leary
*Attorney, Agent, or Firm*—Burton Rodney

[57] ABSTRACT

A method is provided for diagnosing Alzheimer's disease using human blood platelets wherein the presence or absence of functioning calcium-dependent potassium channels in blood platelets are determined by employing potassium channel blockers such as apamin or charybdotoxin, the absence of functioning calcium-dependent potassium channels indicating a positive diagnosis for Alzheimer's disease.

13 Claims, 3 Drawing Sheets

METHOD FOR DIAGNOSING ALZHEIMER'S DISEASE

FIELD OF THE INVENTION

The present invention relates to a method for diagnosing Alzheimer's disease by detecting the presence or absence of functioning calcium-dependent potassium channels in human blood platelets, the absence of such potassium channels indicating a positive diagnosis of Alzheimer's disease.

BACKGROUND OF THE INVENTION

Alzheimer's disease is a progressive neurodegenerative disorder which causes irreversible damage to brain cells leading to dementia and ultimately death. It is characterized by formation of amyloid plaques and neurofibrillary tangles in the brain. Currently, it is primarily diagnosed by exclusion of other known causes of dementia. Diagnosis at an early stage prior to irreversible changes is practically non-existent.

In order for a therapeutic intervention to be significantly effective, it will have to be administered very early on prior to irreversible changes.

Accordingly, a non-invasive diagnostic test for early diagnosis of Alzheimer's disease would be a most welcomed addition to the diagnostician's armamentarium.

Calcium-dependent potassium channels have been found to be implicated with Alzheimer's disease. Abnormalities of potassium ($K^+$) channel function have been reported in cultured cells in Alzheimer's disease (AD)[1].

Depending upon the single channel conductance, a calcium-dependent potassium ($K_{Ca}$) channel is termed high-conductance or maxi-K (100–250 picosiemens (pS)), intermediate-conductance (18–50 pS), or low-conductance (10–14 pS)$K_{Ca}$[2].

The high conductance $K_{Ca}$ is present in neurons, cardiac cells and various types of smooth muscles[3]. The intermediate-conductance channel has been shown to be present in red blood cells[4], and in smooth muscle[5]. The low-conductance channel is present in a variety of cell types[6].

The most important tools to distinguish between low-and high-conductance $K_{Ca}$ are the toxins apamin[7], and charybdotoxin[8].

Atwal, footnote 2 at page 581, points out that "while charybdotoxin specifically blocks maxi-K, apamin is a potent blocker of the low conductance $K_{Ca}$. However, in certain tissues, for example, rat brain, charybdotoxin may block $K_{Ca}$ of all three types."

Mahaut-Smith[8a] discloses that blood platelets contain a 30 pS conductance charybdotoxin-sensitive channel.

It is also known that iberiotoxin specifically inhibits maxi-K channels (Elelvez et al[8b]).

A 113 pS $K^+$channel sensitive to tetraethylammonium has been described as being absent or not functional in cultured fibroblasts from patients with AD[9], and this defect was mimicked in normal fibroblasts by the addition of amyloid beta-protein ($A\beta$)[10], which is also plentiful in platelets[11,12]. However, tetraethylammonium is not a selective inhibitor of $K^+$channels, and so the pharmacological identity of the abnormal channel in cultured fibroblasts is not clear.

U.S. Pat. No. 5,580,748 to Alkon et al (issued Dec, 3, 1996) discloses a method for the diagnosis of Alzheimer's disease using human cells such as fibroblasts, buccal mucosal cells, neurons, and blood cells such as erythrocytes, lymphocytes and lymphoblastoid cells, wherein the absence of a functional 133 pS potassium channel in the test cells indicates the presence of Alzheimer's disease. Tetraethylammonium is employed as a potassium channel blocker to aid in detecting the presence of the functioning 113 pS potassium channel.

DESCRIPTION OF THE INVENTION

In accordance with the present invention, a method is provided for diagnosing Alzheimer's disease which includes the steps of (a) obtaining a sample of platelets from a human subject, and (b) detecting the presence or absence in such platelets of functioning calcium-dependent potassium ($K_{Ca}$) channels, the absence of such functioning $K_{Ca}$ channel indicating a positive diagnosis for Alzheimer's disease.

Detection of the absence of the functioning calcium-dependent potassium channel will be indicated by lack of inhibition by a potassium channel blocker which has the ability to block the functioning $K_{Ca}$ channel, and may, for example, include apamin, charybdotoxin, or a combination thereof, depending upon the specific functioning calcium-dependent potassium channel involved.

In addition, in accordance with the present invention, a method is provided for diagnosing Alzheimer's disease which includes the step of detecting the presence or absence of one or more functioning small-conductance calcium-dependent potassium ($SK_{Ca}$) channels in blood platelets of a human subject, the absence of a functioning $SK_{Ca}$ channel in such platelets indicating a positive diagnosis for Alzheimer's disease.

Detection of the absence of the functioning $SK_{Ca}$ channel will be indicated by lack of inhibition by a $SK_{Ca}$ channel blocker which has the ability to block the functioning $SK_{Ca}$ channel, and may, for example, include apamin, charybdotoxin, or a combination thereof, depending upon the specific $SK_{Ca}$ channel involved.

In addition, in accordance with the present invention, a method is provided for diagnosing Alzheimer's disease which includes the step of detecting the presence or absence of a functioning charybdotoxin-sensitive potassium ($K_{Ch}$) channel in blood platelets of a human subject, the absence of a functioning $K_{Ch}$ channel in such platelets indicating a positive diagnosis for Alzheimer's disease.

Detection of the absence of the functioning $K_{Ch}$ channel will be indicated by lack of inhibition by charybdotoxin which has the ability to block the functioning $K_{Ch}$ channel.

Detection of the presence or absence of the functional $K_{Ca}$ channel, $SK_{Ca}$ channel and/or $K_{Ch}$ channel may be determined by conventional techniques for measuring electrical currents in cells such as the patch clamp technique disclosed by Sakmann, B. et al[28]. The presence or absence of the functional potassium channel may also be detected by (1) loading blood platelets with $^{86}Rb^+$, (2) stimulating $^{86}Rb^+$ efflux (from the platelets via $K_{Ca}$ channels) with thrombin or ionomycin, (3) subjecting the thrombin- or ionomycin-stimulated $^{86}Rb^+$ efflux to the action of an appropriate potassium channel blocker, such as apamin, charybdotoxin or a combination thereof, depending upon the particular functional $K_{Ca}$ channel involved, and (4) determining if the $K_{Ca}$ channel blocker significantly inhibits the thrombin- or ionomycin-stimulated $^{86}Rb^+$ efflux to cause significant reductions in the $^{86}Rb^+$ efflux, a lack of significant inhibition and significant reduction in the $^{86}Rb^+$ efflux indicating a positive diagnosis for Alzheimer's disease.

Thus, where the $K_{Ca}$ channel is a small-conductance calcium dependent potassium ($SK_{Ca}$) channel, the potassium channel blocker employed will preferably be apamin or a combination of apamin and charybdotoxin (weight ratio apamin:charybdotoxin from about 4:1 to about 1:1, preferably from about 3:1 to about 1.5:1).

Where the $K_{Ca}$ channel is a charybdotoxin-sensitive potassium ($K_{Ch}$) channel, the potassium channel blocker employed will be charybdotoxin or a combination of charybdotoxin and apamin (weight ratio charybdotoxin:apamin from about 4:1 to about 1:1, preferably from about 3:1 to about 1.5:1).

EXAMPLE

Figures 1A, 1B:
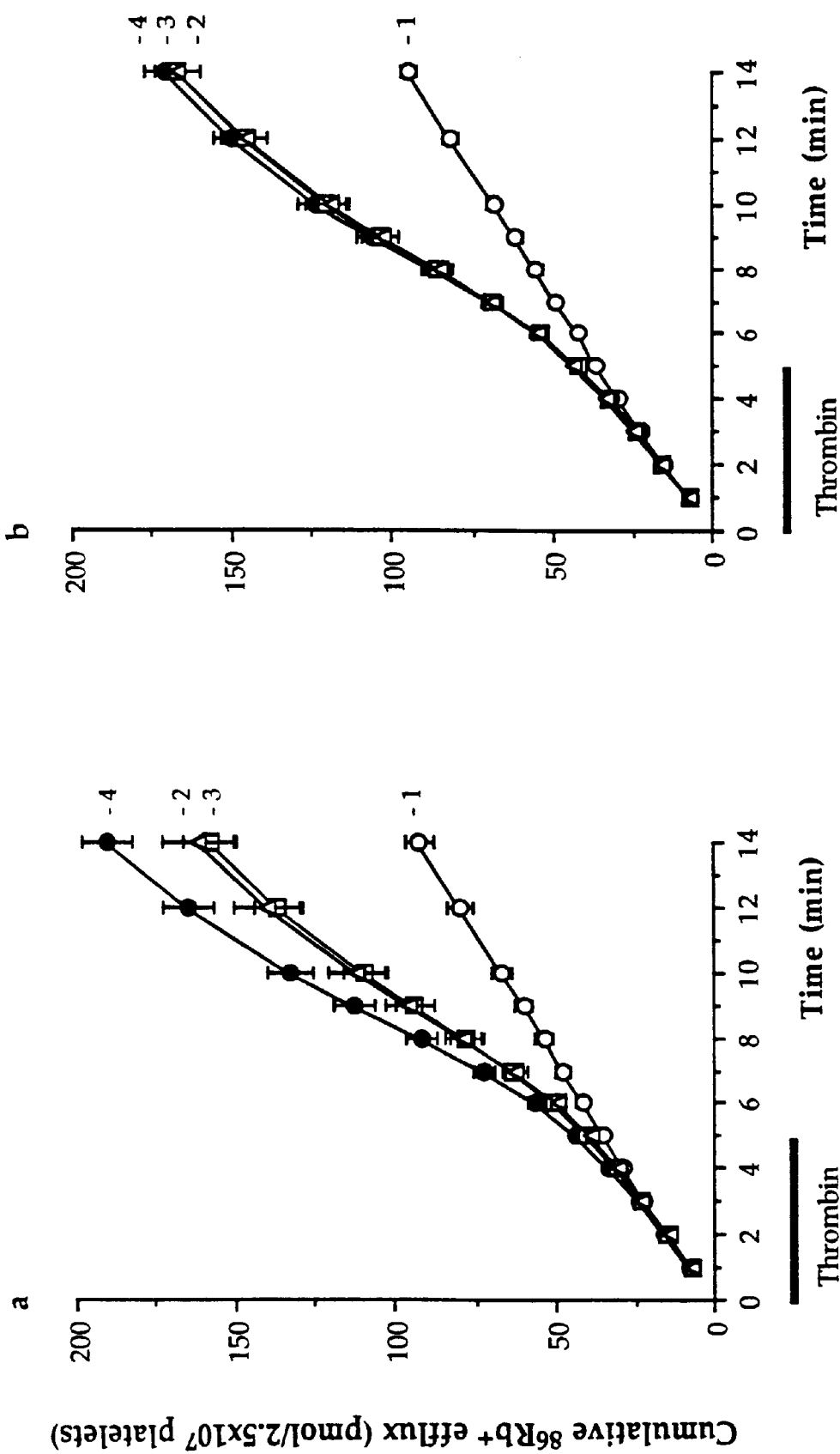
FIGS. 1a and 1b are graphs showing the effects of apamin and charybdotoxin on thrombin-stimulated $^{86}Rb^+$ efflux in Control subjects (FIG. 1a) and in patients with Alzheimer's disease (FIG. 1b)

The following clinical experiments were carried out to determine if there is abnormal function of potassium channels in the platelets of patients with Alzheimer's disease.

Methods

Patient selection. Subjects with and without cognitive dysfunction were rigorously assessed annually, with a full range of blood tests to exclude metabolic or other causes of dementia and to assess cognitive function using the Cambridge Examination for Mental Disorders of the Elderly (CAMDEX)[25].

Diagnoses were made according to criteria of the National Institutes of Neurology and Communicative Disorders-Alzheimer's Disease and Related Disorders Association Work Group (NINCDS-ADRDA)[13] and the criteria described in the Diagnostic and Statistical Manual of Mental Disorders, Third Edition, Revised (DSM-IIIR)[14] in addition to data from CT scans,[15,26] and the SPET regional cerebral blood flow data[15,16]. Those with an OPTIMA (Oxford Project to Investigate Memory and Aging) diagnosis of 'probable AD' not only had no evidence of any other significant metabolic or psychiatric process that was thought to contribute to the dementia, but also had evidence of both significant medial temporal lobe atrophy on CT[26], without evidence of moderate or greater white matter change on axial images, and moderate or greater parietotemporal blood flow deficits on SPET[15,16]. If there was clinical evidence of another process in addition to or other than AD, which the clinician considered could have contributed to the clinical presentation or have given rise to it, then a diagnosis of 'possible AD' was made (four cases, one with ischaemia and three with possible frontal lobe dementia). If, however, the clinical presentation could have been attributed to either AD or another dementia, but the imaging and longitudinal data were highly suggestive of AD on the basis of previously reported necropsy-confirmed cases[16], and overall the clinician's impression was of AD, then a diagnosis of 'probable AD' was made (four cases, two of frontal lobe dementia, one of vascular disease, and one of hypoxia). In six cases the diagnosis was clearly 'probable AD'.

In a previous necropsy-confirmed cohort, the use of these criteria, using CT and SPET changes alone, without taking into account the clinical history or cognitive profile, had a sensitivity of over 85% and a specificity of over 95%[16]. In the cases with 'probable AD' studied in this series, all of whom remain alive, the likelihood that AD accounted for the dementia is thought to be extremely high. Controls were selected to be age-and sex-matched (Table 1), had no evidence of cognitive dysfunction, i.e. their CAMCOG scores were over 79/108[27], complained of no memory problems, and did not have the combination of a minimum medial temporal lobe width on CT of less than the fifth centile for controls of the same age with a moderate or greater parietotemporal perfusion deficit on SPET. Subjects recruited as part of OPTIMA were 14 patients with dementia of the Alzheimer type and 14 non-demented age- and sex-matched controls (details in Table 1); each experiment was performed on 11 or 12 of these individuals.

Platelet perfusion[17]. Blood was drawn by venepuncture and anticoagulated with acid-citratedextrose (ACD). Platelets were prepared by centrifugation within an hour of venesection and incubated with $^{86}Rb^+$ for 2 h. The platelet suspension ($2.5 \times 10^7$ platelets per ml) was then injected into perfusion chambers, where the cells settled and became immobilized on inert filters (Millipore). The platelets were then continuously perfused with Krebs solution, to allow them to stabilize for 20 min before the start of each experiment. The perfusion buffer was then changed for 5 min to Krebs solution containing thrombin (0.3 IU/ml) or ionomycin (1 μM), after which the perfusion was switched to the original solution and continued for another 20 min. From 0 to 10 min after the addition of thrombin or ionomycin the perfusate was collected at 1-min intervals and thereafter at 2-min intervals. The solutions used for perfusion were bubbled with 95% $O_2$ and 5% $CO_2$ throughout the experiment (pH 7.4). At the end of the experiment the polycarbonate filters were retrieved and placed in scintillation vials, to which 3.5 ml of Aquasafe 500 scintillation fluid was added. The radioactivity in the perfusates and filters was determined by liquid scintillation counting in a Beckmann LS 6000 SE counter and the loss of radioactivity from the cells was calculated. The amount of $^{86}Rb^+$ (pmol) in each fraction of perfusate collected was determined using the specific activity of the isotope. The radioactivity was measured in each fraction and the results were plotted as the cumulative efflux of $^{86}Rb^+$ against time.

Buffers and drucas. ACD contained citric acid (15 g), trisodium citrate (25 g), and dextrose (20 g) in 1 l of distilled water. Krebs buffer contained (mmol/l): NaCl (119); KCl (4.6); $CaCl_2$ (1.5); $NaH_2PO_4$ (1.2); $MgCl_2$ (1.2); $NaHCO_3$ (15); and glucose (11). Apamin, charybdotoxin, α-dendrotoxin, iberiotoxin, ionomycin, and human thrombin were purchased from Sigma Chemical Company, Poole, Dorset. $^{86}RbCl$ was purchased from Amersham International plc (Amersham, Bucks).

Thrombin and ionomycin. Solutions of thrombin were prepared freshly in distilled water for each experiment and further diluted to a concentration of 0.3 IU/ml in Krebs solution. Stock solutions of ionomycin (10 mM in dimethylsulphoxide) were prepared and stored in aliquots at 4° C. On the day of the experiment ionomycin was further diluted in Krebs solution to a concentration of 1 μM.

Apamin, charybdotoxin, iberiotoxin, and α-dendrotoxin. Apamin, charybdotoxin, iberiotoxin, and α-dendrotoxin were freshly prepared for each experiment. Apamin, (100 nM), charybdotoxin (300 nM), iberiotoxin (300 nM), and α-dendrotoxin (200 nM) were reconstituted in distilled water and stored in aliquots at −20° C. On the day of the experiment the toxins were further diluted in Krebs solution. Apamin was pre-incubated with the platelets (added at time −20 min) and charybdotoxin, iberiotoxin, and α-dendrotoxin were added with thrombin (at 0 min) for a period of 5 min.

Data Dresentation and analysis. The results in FIGS. 1–3 are shown as cumulative effluxes of $^{86}Rb^+$ from 0 to 14 min. The data are shown as means±SEMs (n=number of experiments with platelets obtained from different volunteers). The efflux data were analyzed using analysis of variance with repeated measures.

$K^+$ channel fluxes. Platelets were prepared and their $K^+$ channel fluxes studied as described by DeSilva, H. A. et al[17], by loading fresh platelets with $^{86}Rb^+$ (used as a radioactive analogue of $K^+$)[18,19] and stimulating $^{86}Rb^+$ efflux with thrombin and ionomycin. It has already been shown that thrombin and ionomycin stimulate $^{86}Rb^+$ efflux from platelets via $K^+$ channels, and that the efflux occurs via $K_{Ca}$ channels, sensitive to the highly selective inhibitors apamin and charybdotoxin (i.e. small-conductance calcium-dependent, $SK_{Ca}$, channels and charybdotoxin-sensitive, $K_{Ch}$, channels), and via voltage-gated ($K_v$) channels, sensitive to α-dendrotoxin[20,21].

Uptake of rubidium by platelets. The uptake of $^{86}Rb^+$ by the platelets was the same in both groups (not shown).

Since over 90% of this uptake in platelets is inhibitable by ouabain and attributable to the sodium/potassium pump (de Silva & Aronson, unpublished observations), this result suggests that the sodium/potassium pump functions normally in AD.

Non-stimulated $^{86}Rb^+$ efflux. Non-stimulated cumulative $^{86}Rb^+$ efflux was linear with time (open circles; FIGS. 1–3) and did not differ between AD patients and controls. This efflux is partly mediated by the $Na^+/K^+/2Cl^-$-co-transport system[17].

Thrombin-stimulated 86Rb$^+$ efflux. FIG. 1a and 1b show the effects of apamin and charybdotoxin on thrombin-stimulated $^{86}Rb^+$ efflux. FIG. 1a relates to Control subjects, and shows that thrombin 0.3 IU/ml (4-filled circles) increased $^{86}Rb^+$ efflux over the non-stimulated efflux (1-open circles). Apamin 100 nM (3-open squares) and charybdotoxin 300 nM (2-open triangles) inhibited the stimulated $^{86}Rb^+$ efflux (n=11; P<0.0001).

FIG. 1b relates to patients with Alzheimer's disease and shows that thrombin 0.3 IU/ml (4-filled circles) increased $^{86}Rb^+$ efflux over the non-stimulated efflux (1-open circles) to the same extent as in controls (P=0.996). Apamin 100 nM (3-open squares) and charybdotoxin 300 nM (2-open triangles) had no significant effect on the stimulated $^{86}Rb^+$ efflux (n=12; P=0.941).

Figures 2A, 2B:
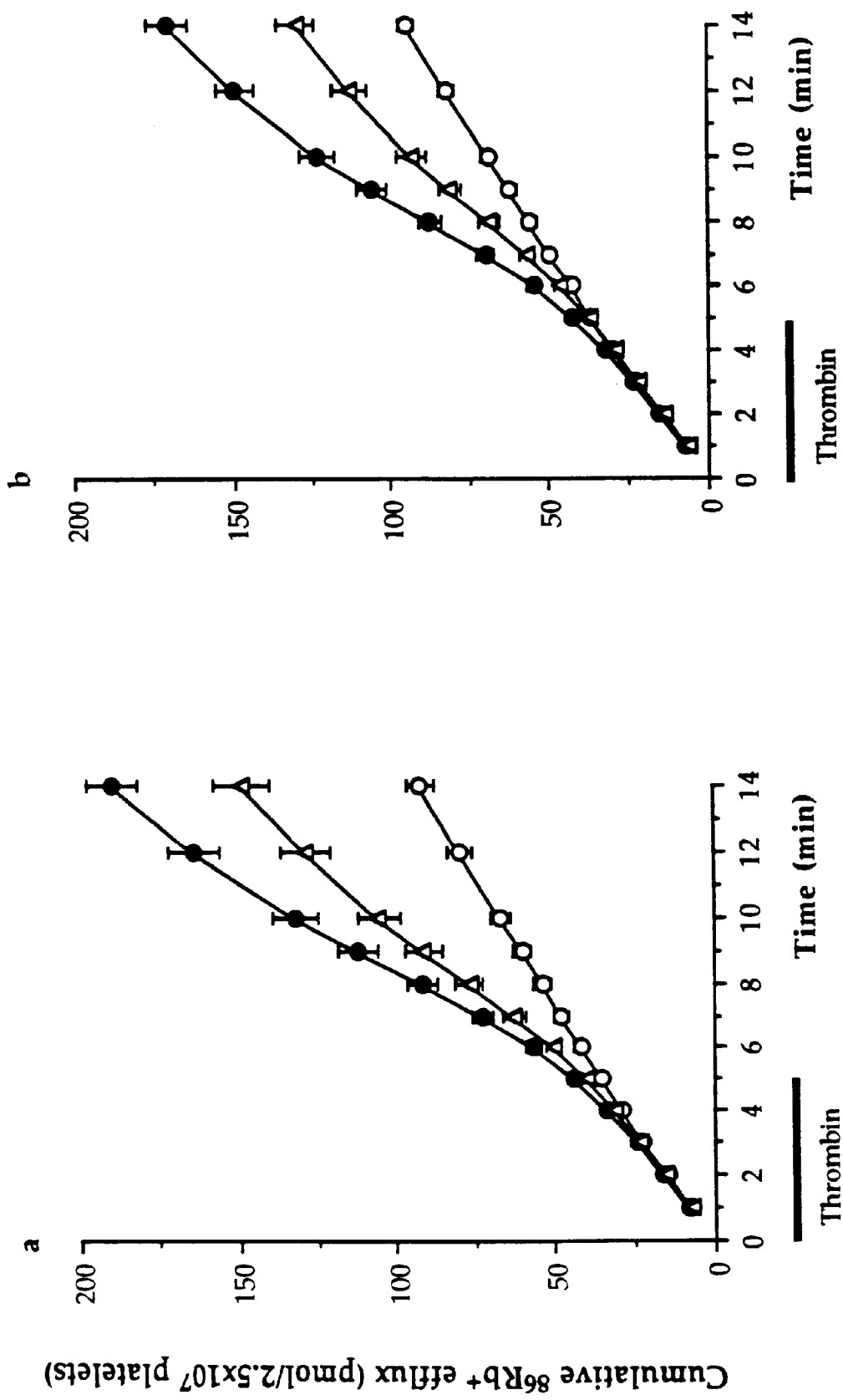
FIGS. 2a and 2b are graphs showing the effect of α-dendrotoxin on thrombin-stimulated $^{86}Rb^+$ ef flux in Control subjects (FIG. 2a) and in patients with Alzheimer's disease (FIG. 2b)

FIGS. 2a and 2b show the effect of α-dendrotoxin on thrombin-stimulated $^{86}Rb^+$ efflux. FIG. 2a relates to Control subjects and shows that thrombin 0.3 IU/ml (filled circles) increased $^{86}Rb^+$ efflux over the non-stimulated efflux (open circles). α-dendrotoxin 200 nM (open triangles) inhibited the thrombin-stimulated efflux (n=11; P<0.0001). FIG. 2b relates to patients with Alzheimer's disease and shows that thrombin 0.3 IU/ml (filled circles) increased $^{86}Rb^+$ efflux over the non-stimulated efflux (open circles). α-dendrotoxin 200 nM (open triangles) inhibited the thrombin-stimulated efflux (n=12; P<0.0001).

Control subjects. In control subjects, thrombin stimulated an increase in $^{86}Rb^+$ efflux from platelets (FIGS. 1a and 2a). In 8 of 11 control subjects, apamin and charybdotoxin inhibited the thrombin-stimulated $^{86}Rb^+$ efflux by at least 18% and 16% respectively, while in the other three subjects these toxins had minimal effects (less than 10% inhibition). When the data from all the control subjects were pooled, both apamin and charybdotoxin caused significant reductions in $^{86}Rb^+$ efflux (FIGS. 1a; Table 2). In addition, α-dendrotoxin inhibited thrombin-stimulated $^{86}Rb^+$ efflux from the platelets of all the controls (FIG. 2a; Table 2). These results are similar to the effects of these toxins on thrombin-stimulated $^{86}Rb^+$ efflux in the platelets of young volunteers[20,21], and they confirm that there are $SK_{Ca}$, $K_{Ch}$, and $K_v$ channels in normal human platelets.

Alzheimer's disease. Thrombin also stimulated $^{86}Rb^+$ efflux from the platelets of 12 patients with AD (FIGS. 1b and 2b), to the same extent as in controls (cf. FIGS. 1a and 2a with FIGS. 1b and 2b). In contrast to the results in controls, apamin and charybdotoxin had minimal effects on thrombin-stimulated $^{86}Rb^+$ efflux (less than 10% inhibition) in 9 of 12 patients with AD, while in the other three patients each toxin inhibited the thrombin-stimulated efflux by at least 16%. When the data from all the patients with AD were pooled, neither apamin nor charybdotoxin caused significant reductions in $^{86}Rb^+$ efflux (FIG. 1b; Table 2). In contrast, α-dendrotoxin inhibited the thrombin-stimulated $^{86}Rb^+$ efflux from the platelets of all the patients with AD (FIG. 2b; Table 2).

Ionomvcin-stimulated $^{86}Rb^+$ efflux.

Figures 3A, 3B:
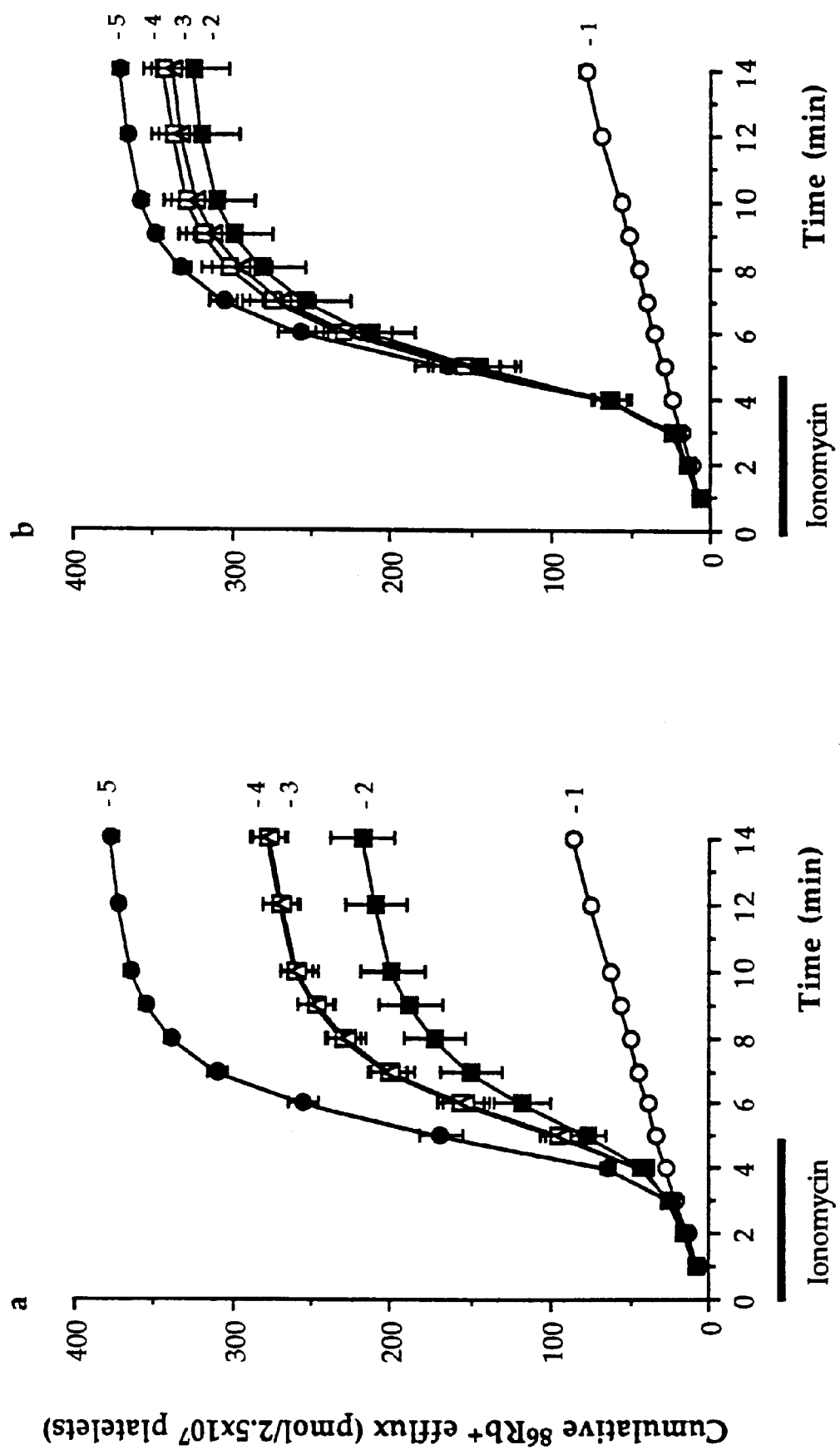
FIGS. 3a and 3b are graphs showing the effect of apamin and charybdotoxin on ionomycin-stimulated $^{86}Rb^+$ efflux in Control subjects (FIG. 3a) and in patients with Alzheimer's disease (FIG. 3b).

FIGS. 3a and 3b show effect of apamin and charybdotoxin on ionomycin-stimulated $^{86}Rb^+$ efflux.

As seen in FIG. 3a, Control subjects; Ionomycin 1 μM (5-filled circles) increased $^{86}Rb^+$ efflux over the non-stimulated efflux (1-open circles). Apamin 100 nM (4-open squares) and charybdotoxin 300 nM (3-open triangles) inhibited the stimulated $^{86}Rb^+$ efflux (P <0.0001). Apamin and charybdotoxin combined (2-filled squares) inhibited the stimulated efflux more than either toxin alone (n=11; P<0.0001).

As seen in FIG. 3b, Alzheimer's disease; Ionomycin 1 μM (5-filled circles) stimulated $^{86}Rb^+$ efflux over the non-stimulated efflux (1-open circles) to the same extent as in controls (P=0.960). Apamin 100 nM (4-open squares) and charybdotoxin 300 nM (3-open triangles), either alone or in combination (2-filled squares), had no significant effect on the stimulated $^{86}Rb^+$ efflux (n=11; P=0.883).

Control subjects. In 9 of 11 control subjects, apamin and charybdotoxin inhibited the ionomycin-stimulated $^{86}Rb^+$ efflux by at least 18% and 22% respectively, while in two subjects these toxins had minimal effects (less than 12% inhibition). When the data from all the controls were pooled, both apamin and charybdotoxin caused significant reductions in $^{86}Rb^+$ efflux (FIG. 3a; Table 2). The two toxins combined had a greater effect than either toxin alone (FIG. 3a; Table 2). These results are similar to those seen in young volunteers[20,21], and they confirm the presence of $SK_{Ca}$ and $K_{Ch}$ channels in human platelets.

Alzheimer's disease. Ionomycin also stimulated $^{86}Rb^+$ efflux from the platelets of 11 patients with AD (FIG. 3b), to the same extent as in controls (cf. FIGS. 3a and 3b). However, apamin, charybdotoxin, and their combination had minimal effects on the ionomycin-stimulated $^{86}Rb^+$ efflux in 8 of 11 patients with AD (less than 12% inhibition). When the data from all the patients with AD were pooled, apamin and charybdotoxin, either alone or in combination, had minimal effects on $^{86}Rb^+$ efflux (FIG. 3b; Table 2).

Although abnormalities of $K^+$ channels have been reported in AD in neural cells (reduced post-mortem binding of $^{125}I$-apamin to hippocampal neurones[22]) and in fibroblasts (absence of a 113 pS channel sensitive to tetraethylammonium[9]), this study is the first to show functional abnormalities of $K^+$ channels in the platelets of response to both thrombin and ionomycin were quantitatively normal in AD, and the thrombin-stimulated efflux showed normal sensitivity to inhibition with α-dendrotoxin, suggesting that the $K_v$ channels are normal in platelets in AD. However, the lack of inhibition of both thrombin-stimulated and ionomycin-stimulated effluxes by apamin and charybdotoxin suggests either that the $SK_{Ca}$ and $K_{Ch}$ channels are not present in platelets in AD or, if they are present, that they are not sensitive to inhibition by these toxins.

If $SK_{Ca}$ and $K_{Ch}$ channels are present in platelets in AD, but unresponsive to inhibition, that would be consistent with the observation that the binding of $^{125}$I-apamin is reduced in post-mortem hippocampal neurones in AD[22]. This might be due to a change in the structure of the binding sites of the inhibitors. Alternatively, it might be due to an abnormality of the specific interaction of calcium with the channels, since the efflux stimulated by ionomycin, which increases the intracellular concentration of calcium, was not inhibitable. Furthermore, the $K_v$ channels were not affected, suggesting that $K_{Ca}$ channels are selectively impaired in AD.

Alternatively, $SK_{Ca}$ and $K_{Ch}$ channels may not be present at all in AD. However, if that is so, then $^{86}Rb^+$ efflux must be occurring through other $K^+$ channels, since the thrombin-stimulated and ionomycin-stimulated effluxes were quantitatively normal. However, normal human platelets do not contain large-conductance calcium-dependent ($BK_{Ca}$) channels[21], and iberiotoxin, a selective inhibitor of $BK_{Ca}$ channels, had no effect on ionomycin-stimulated effluxes in platelets from any individual (Table 2), while the only other type of $K^+$ channel found in platelets, $K_v$ channels[20,21], responded normally to α-dendrotoxin. These observations argue against upregulation of other normal channels in AD. On the other hand, metabolites of the beta-amyloid precursor protein (β-APP) are capable of de novo formation of $K^+$ channels[23] that are insensitive to some inhibitors[1], and the $^{86}Rb^+$ efflux detected in AD might be via such channels.

Absence or non-functionality of the $K_{Ca}$ channels might also explain the observation[24] that platelets from patients with AD had a higher thrombin-stimulated rise in intracellular $Ca^{2+}$, since that might represent an exaggerated attempt to switch on non-existent or non-functional channels.

The frequencies of alleles ε2, ε3, and ε4 of the apolipoprotein E gene in the patients and controls are shown in Table 3. As expected, significantly more patients with AD had one or two ε4 alleles. Nine of the 13 individuals (patients and controls) who had one or two ε4 alleles had abnormalities of inhibition of $K_{Ca}$ channels, compared with only five of the 15 who had no ε4 alleles (P=0.06), suggesting a link between the $K^+$ channel abnormalities and the presence of the ε4 allele. No such relationship was found between the $K^+$ channel abnormalities and either the ε2 or the ε3 allele.

In conclusion, there were abnormalities of inhibition of $SK_{Ca}$ and $K_h$ channels in the platelets of patients with AD compared with matched controls. Thus, $K_{Ca}$ channel abnormalities provide a marker for patients with AD.

TABLE 1

Patient data.
The data are given as mean (sd). There were no significant differences between the groups.

| Measure | Alzheimer's disease (n = 14) | Controls (n = 14) |
|---|---|---|
| Age (y) 67.1 (7.5) | 67.9 (7.7) | |
| Sex (M/F) | 9/5 | 9/5 |
| Systolic blood pressure (mmHg) | 154 (16) | 140 (15) |
| Diastolic blood pressure (mmHg) | 90 (14) | 81 (14) |
| Serum Sodium (mM) | 139 (3) | 139 (2) |
| Serum potassium (mM) | 3.9 (0.4) | 4.0 (0.3) |
| Serum Calcium (mM) | 2.43 (0.10) | 2.32 (0.13) |
| Serum urea (M) | 5.7 (1.3) | 6.3 (2.7) |
| Serum creatinine (μM) | 104 (12) | 103 (24) |
| Blood glucose (mM) | 5.9 (2.1) | 5.6 (1.1) |
| Platelet count (×10⁹/l) | 233 (58) | 233 (62) |
| Haemoglobin (g/dl) | 13.9 (0.8) | 14.2 (1.1) |
| Mean cell volume (fl) | 89 (4) | 90 (5) |
| White cell count (×10⁹/l) | 6.9 (1.5) | 6.5 (1.5) |
| Total serum cobalamins (ng/l) | 270 (90) | 315 (125) |

TABLE 2

Inhibition of thrombin-stimulated and ionomycin-stimulated $^{86}Rb^+$ effluxes by apamin, charybdotoxin, α-dendrotoxin, and iberiotoxin in platelets of patients with AD and age- and sex-matched controls. Data are given as median (interquartile range) percentages. Statistical comparisons by rank sum tests.

| Toxin | Inhibition in controls (%) | Inhibition in Alzheimer's disease (%) | P value |
|---|---|---|---|
| Thrombin-stimulated $^{86}Rb^+$ efflux | | | |
| Apamin | 26 (20–27) | 0 (0–0) | <0.01 |
| charybdotoxin | 22 (18–29) | 0 (0–4) | <0.01 |
| α-dendrotoxin | 26 (20–29) | 19 (18–27) | NS |
| Ionomycin-stimulated $^{86}Rb^+$ efflux | | | |
| Apamin | 30 (20–31) | 1 (0–20) | <0.01 |
| Charybdotoxin | 28 (20–34) | 4 (1–26) | <0.01 |
| Apamin + Charybdotoxin | 51 (34–52) | 2 (0–40) | <0.01 |
| Iberiotoxin | 2 (0–3) | 0 (0–4) | NS |

TABLE 3

Numbers of normal and abnormal results in patients and controls. An abnormal result was defined as less than 15% inhibition by apamin and charybdotoxin. Statistical comparisons were by chi-square test. For comparison the distributions of apolipoprotein E alleles in the two groups are also shown.

| Agonist | | Alzheimer's disease | Controls | P value |
|---|---|---|---|---|
| Thrombin | No. with an abnormal result | 9 | 3 | |
| | | | | <0.02* |
| | No. with a normal result | 3 | 8 | |
| Ionomycin | No. with an abnormal result | 9 | 3 | |
| | | | | =0.01* |

TABLE 3-continued

Numbers of normal and abnormal results in patients and controls. An abnormal result was defined as less than 15% inhibition by apamin and charybdotoxin. Statistical comparisons were by chi-square test. For comparison the distributions of apolipoprotein E alleles in the two groups are also shown.

| Agonist | disease | Alzheimer's Controls | value | P |
|---|---|---|---|---|
| | No. with a normal result | 2 | 8 | |
| Apolipoprotein E allele frequencies | | | | |
| ε2/2 | | 0 | 2 | |
| ε2/3 | | 1 | 0 | |
| ε3/3 | | 4 | 8 | <0.03† |
| ε3/4 | | 5 | 4 | |
| ε4/4 | | 4 | 0 | |

*chi-squared test
†chi-squared test for trend

REFERENCES

1. Fraser, S. P. et al, Ionic effects of the Alzheimer's disease β-amyloid precursor protein and its metabolic fragments. Trends Neurosci. 20, 67–72 (1997).

2. K. Atwal, Med. Res. Rev. 12, 6, 579; N. S. Cook, Trends Pharmacol. Sci. 9, 21 (1988).

3. J. J. Singer et al, Pflügers Archiv. 408, 98 (1987), I. Baro et al, Pflügers Archiv. 414, Suppl. 1), S168 (1989); and F. Ahmed et al, Br. J. Pharmacol. 83, 227 (1984).

4. O. P. Hamil et al, Pflügers Archiv. 391, 85 (1981).

5. R. Inoue et al, Pflügers Archiv. 406, 138 (1986).

6. R. Inoue et al, Pflügers Archiv. 405, 173 (1985); G. Isenberg et al, Pflügers Archiv. 405, R62 (1986); and N. S. Cook et al, J. Physiol. 358, 373 (1985).

7. B. Marqueze et al, Eur. J. Biochem. 169, 295 (1987).

8. G. Gimenez et al, Proc. Natl. Acad. Sci. U.S.A. 85, 3329 (1988).

8a. Mahaut-Smith M. P., Calcium-activated potassium channels in human platelets, J. Physiol. 1995; 484:15–24.

8b. Galvez et al, Purification and characterization of a unique, potent, peptidyl probe for the high conductance calcium-activated potassium channel from the venom of the scorpion Buthus tamulus, J. Biol. Chem. 1990; 265:11083–90.

9. Etcheberrigaray, R. et al, Potassium channel dysfunction in fibroblasts identifies patients with Alzheimer's disease. Proc. Natl. Acad. Sci. USA 90, 8209–8213 (1993).

10. Etcheberrigaray, R. et al, Soluble β-amyloid induction of Alzheimer's phenotype for human fibroblast K+ channels. Science 264, 276–279 (1994).

11. Van Nostrand, W. E. et al, Protease nexin-II (amyloid beta-protein precursor): a platelet alpha granule protein. Science 248, 745–748 (1990).

12. Chen, M., et al, Platelets are the primary source of amyloid β-peptide in human blood. Biochem. Biophys. Res. Comm. 213, 96–103 (1995).

13. McKhann, G. et al, Clinical diagnosis of Alzheimer's disease: report of the NINCDS-ADRDA work group under the auspices of Department of Health and Human Services Task Force on Alzheimer's Disease. Neurology 34, 939–944 (1984).

14. American Psychiatric Association. Diagnostic and Statistical Manual of Mental Disorders. 3rd Revised ed. Washington: American Psychiatric Association (1987).

15. Jobst, K. A. et al, Association of atrophy of the medial temporal lobe with reduced blood flow in the posterior parietotemporal cortex in patients with a clinical and pathological diagnosis of Alzheimer's disease. J. Neurol. Neurosurg. Psychiatry 55, 190–194 (1992).

16. Jobst, K. A. et al, on behalf of OPTIMA. Accurate prediction of confirmed Alzheimer's disease and the differential diagnosis of dementia: the use of $^{99m}$Tc-HMPAO SPET and X-ray CT in medial temporal lobe dementias. Int. Psychogeriatr. In press (1997).

17. De Silva, H. A. et al, Effects of high external concentrations of potassium on $^{86}$rubidium efflux in human platelets: evidence for Na$^+$/K$^+$/2Cl$^-$ co-transport. Clin. Sci. 91, 725–731 (1996).

18. de Allie, F. A. et al, Characterization of Ca$^{2+}$-activated $^{86}$Rb$^+$ fluxes in rat C6 glioma cells: a system for identifying novel IK$_{Ca}$-channel toxins. Br. J. Pharmacol. 117, 479–487 (1996).

19. Andersson, T. G. L. et al, The efflux of $^{86}$Rb$^+$ and [$^3$H]5-HT from human platelets during continuous perfusion: effects of potassium-induced membrane depolarization and thrombin stimulation. Acta Physiol. Scand. 141, 421–428 (1991).

20. De Silva, H. A. et al, Evidence for calcium-dependent (K$_{Ca}$) and voltage-dependent (K$_v$) potassium channels in human platelets. Pharmacologist 39, 57 (1997).

21. De Silva, H. A. et al, Pharmacological evidence of calcium-activated and voltage-gated potassium channels in human platelets. Clin. Sci. 1997,; 93:249–55.

22. Ikeda, M. et al, Selective reduction of [$^{125}$I]apamin binding sites in Alzheimer hippocampus: a quantitative autoradiographic study. Brain Res. 567, 51–56 (1991).

23. Furukawa, K. et al, Activation of K$^+$ channels and suppression of neuronal activity by secreted β-amyloid precursor protein. Nature 379, 74–78 (1996).

24. Hajimohammadreza, I. et al, Platelet and erythrocyte membrane changes in Alzheimer's disease. Biochim. Biophys. Acta 1025, 208–214 (1990).

25. Roth, M. et al, CAMDEX The Cambridge Examination for Mental Disorders of the Elderly. Cambridge: Cambridge University Press (1988).

26. Jobst, K. A. et al, Detection in life of confirmed Alzheimer's disease using a simple measurement of medial temporal lobe atrophy by computed tomography. Detection in life of confirmed Alzheimer's disease using a simple measurement of medial temporal lobe atrophy by computed tomography. Lancet 340, 1179–1183 (1992).

27. Roth, M. et al, CAMDEX—a standardized instrument for the diagnosis of mental disorder in the elderly with special reference to the early detection of dementia. Br. J. Psychiatry 149, 698–709 (1986).

28. Sakmann, B. et al, (1984) Annual Review of Physiology 46:455.

What is claimed is:

1. A method for diagnosing Alzheimer's disease, which comprises obtaining a sample of platelets from a human subject, and detecting the presence or absence of functioning calcium-dependent potassium (K$_{Ca}$) channels of specified slope conductance in said platelets, the absence of said functioning K$_{Ca}$ channel indicating a positive diagnosis for Alzheimer's disease.

2. The method as defined in claim 1 wherein the absence of said functioning K$_{Ca}$ channel is indicated by lack of inhibition by a potassium channel blocker which has the ability to block the functioning $K_{C_a}$ channel.

3. The method as defined in claim 2 wherein the potassium channel blocker is apamin or charybdotoxin or a combination thereof.

4. The method as defined in claim 1 wherein the presence or absence of the calcium-dependent potassium channel is determined by (1) loading blood platelets with $^{86}Rb^+$, (2) stimulating $^{86}Rb^+$ efflux from the platelets via $K_{C_a}$ channels with thrombin or ionomycin, (3) subjecting the thrombin- or ionomycin-stimulated $^{86}Rb^+$ efflux to the action of a potassium channel blocker, and (4) determining if the potassium channel blocker significantly inhibits the thrombin- or ionomycin-stimulated $^{86}Rb^+$ efflux to cause significant reductions in the $^{86}Rb^+$ efflux, a lack of significant inhibition and significant reduction in the $^{86}Rb^+$ efflux indicating a positive diagnosis for Alzheimer's disease.

5. A method for diagnosing Alzheimer's disease, which comprises detecting the presence or absence of one or more functioning small-conductance calcium-dependent potassium ($SK_{C_a}$) channels in blood platelets of a human subject, the absence of a functioning $SK_{C_a}$ channel in such platelets indicating a positive diagnosis for Alzheimer's disease.

6. The method as defined in claim 5 wherein the absence of a functioning $SK_{C_a}$ channel is indicated by lack of significant inhibition by a $SK_{C_a}$ channel blocker which has the ability to block the functioning $SK_{C_a}$ channel.

7. The method as defined in claim 6 wherein the potassium channel blocker is apamin.

8. The method as defined in claim 6 wherein the potassium channel blocker is a combination of apamin and charybdotoxin.

9. The method as defined in claim 5 wherein the presence or absence of the SKCa channel is determined by (1) loading blood platelets with $^{86}Rb^+$, (2) stimulating $^{86}Rb^+$ efflux (from the platelets via $K_{C_a}$ channels) with thrombin or ionomycin, (3) subjecting the thrombin- or ionomycin-stimulated $^{86}Rb^+$ efflux to the action of a $SK_{C_a}$ channel blocker, and (4) determining if the $SK_{C_a}$ channel blocker significantly inhibits the thrombin- or ionomycin-stimulated $^{86}Rb^+$ efflux to cause significant reductions in the $^{86}Rb^+$ efflux, a lack of significant inhibition and significant reduction in the $^{86}Rb^+$ efflux indicating a positive diagnosis for Alzheimer's disease.

10. A method for diagnosing Alzheimer's disease, which comprises detecting the presence or absence of a functioning charybdotoxin-sensitive potassium ($K_{Ch}$) channel in blood platelets of a human subject, the absence of a functioning $K_{Ch}$ channel in such platelets indicating a positive diagnosis for Alzheimer's disease.

11. The method as defined in claim 10 wherein the absence of a functioning $K_{Ch}$ channel is indicated by lack of significant inhibition by charybdotoxin which has the ability to block the functioning $K_{Ch}$ channel.

12. The method as defined in claim 10 wherein the absence of a functioning $K_{Ch}$ channel is indicated by lack of significant inhibition by a combination of charybdotoxin and apamin.

13. The method as defined in claim 10 wherein the presence or absence of the charybdotoxin-sensitive channel is determined by (1) loading blood platelets with $^{86}Rb^+$, (2) stimulating $^{86}Rb^+$ efflux (from the platelets via $K_{C_a}$ channels) with thrombin or ionomycin, (3) subjecting the thrombin- or ionomycin-stimulated $^{86}Rb^+$ efflux to the action of a $K_{Ch}$ channel blocker, and (4) determining if the $K_{Ch}$ channel blocker significantly inhibits the thrombin- or ionomycin-stimulated $^{86}Rb^+$ efflux to cause significant reductions in the $^{86}Rb^+$ efflux, a lack of significant inhibition and significant reduction in the $^{86}Rb^+$ efflux indicating a positive diagnosis for Alzheimer's disease.

* * * * *